US010102335B2

(12) United States Patent
Fisher et al.

(10) Patent No.: US 10,102,335 B2
(45) Date of Patent: Oct. 16, 2018

(54) COST-OPTIMIZED DESIGN ANALYSIS FOR RAPID MICROBIAL PROTOTYPING

(71) Applicant: Virginia Commonwealth University, Richmond, VA (US)

(72) Inventors: Adam Fisher, Richmond, VA (US); J. Paul Brooks, Richmond, VA (US); Stephen S. Fong, Mechanicsville, VA (US)

(73) Assignee: Virginia Commonwealth University, Richmond, VA (US)

( * ) Notice: Subject to any disclaimer, the term of this patent is extended or adjusted under 35 U.S.C. 154(b) by 1053 days.

(21) Appl. No.: 14/134,353

(22) Filed: Dec. 19, 2013

(65) Prior Publication Data

US 2014/0172318 A1     Jun. 19, 2014

Related U.S. Application Data

(60) Provisional application No. 61/739,154, filed on Dec. 19, 2012.

(51) Int. Cl.
*G06F 19/18*   (2011.01)
*G06F 19/12*   (2011.01)
*G06F 19/10*   (2011.01)

(52) U.S. Cl.
CPC .............. *G06F 19/18* (2013.01); *G06F 19/12* (2013.01)

(58) Field of Classification Search
None
See application file for complete search history.

(56) References Cited

U.S. PATENT DOCUMENTS

| | | | |
|---|---|---|---|
| 2004/0029149 A1* | 2/2004 | Palsson | G06F 19/12 435/6.14 |
| 2007/0038419 A1 | 2/2007 | Usuda et al. | |
| 2013/0095566 A1 | 4/2013 | Oltvai et al. | |

OTHER PUBLICATIONS

Akashi H and Gojobori T, Metabolic efficiency and amino acid composition in the proteomes of *Escherichia coli* and *Bacillus subtilis*. PNAS, Mar. 19, 2002, vol. 99, No. 6, pp. 3695-3700.
Burgard et al., "Optknock: a bilevel programming framework for identifying gene knockout strategies for microbial strain optimization", Biotechnology and Bioengineering, 2003, vol. 84, pp. 647-657.
Covert MW et al., "Regulation of gene expression in flux balance models of metabolism", Journal of Theoretical Biology, vol. 213, Issue 1, Nov. 7, 2001, pp. 73-88.
Ebrahim, A. et al., "COBRApy: COnstraints-Based Reconstruction and Analysis for Python", 2013, BMC Systems Biology, vol. 7:74, 6 pages, pp. 1-6.
Edwards, JS et al., "Systems properties of the Haemophilus influenzae Rd metabolic genotype", The Journal of Biological Chemistry, vol. 274, No. 25, Jun. 18, 1999, pp. 17410-17416.
Jol SJ, et al., "Thermodynamic calculations for biochemical transport and reaction processes in metabolic networks", Biophysical Journal, vol. 99, Nov. 2010, pp. 3139-3144.
Orth et al., "What is flux balance analysis", Nature Biotechnology, 2010, vol. 28(3), pp. 245-248.
Papin JA, et al. "Topological analysis of mass-balanced signaling networks: a framework to obtain network properties including crosstalk", Journal of Theoretical Biology, vol. 227, 2004, pp. 283-297.
Pharkya, P. et al., "OptStrain: a computational framework for redesign of microbial production systems", Genome Research, Nov. 2004, vol. 14(11), pp. 2367-2376.
Price ND et al., "Genome-scale microbial in silico models: the constraints-based approach", Trends in Biotechnology, vol. 21, Issue 4, Apr. 2003, pp. 162-169.
Reed JL et al., "An expanded genome-scale model of *Escherichia coli* K-12 (iJR904 GSM/GPR)", Genome Biology, 2003, vol. 4, Issue 9, Article R54, pp, 1-12.
Schellenberger et al., "Quantitative prediction of cellular metabolism with constraint-based models: the COBRA Toolbox v2.0", Nature Protocols, 2011, vol. 6, pp. 1290-1307.
Schilling CH et al., "Towards metabolic phenomics: Analysis of genomic data using flux balances", Biotechnology Progress, 1999, vol. 15, pp. 288-295.
Schuetz R, et al., "Multidimensional optimality of microbial metabolism", Science, vol. 336(6081), pp. 601-604.
Varma, A. et al., "Metabolic Flux Balancing: Basic concepts, Scientific and Practical Use", Nature Bio/Technology, 1994;12:994-8.

\* cited by examiner

*Primary Examiner* — Lori A. Clow
(74) *Attorney, Agent, or Firm* — New River Valley IP Law, P.C.; Michele L. Mayberry; Timothy D. Nolan (57) ABSTRACT

Computer-implemented methods for providing improvements in genome-scale metabolic models are described. The methods identify and optimize metabolic flux states that minimize the cost of enzyme production while maximizing a desired cellular phenotype. The computer-implemented methods may maximize cellular phenotypes such as growth (biomass) or production of a metabolite, such as a commercially valuable chemical compound, through the selection of metabolic pathways that maximize these phenotypes while minimizing metabolic costs associated with production of the proteomic constituents of individual metabolic pathways. The computer implemented methods may be useful for computationally designing microbial strains for the production of chemicals.

14 Claims, 9 Drawing Sheets

| Amino acid | Symbol | Cost (phosphate bond equivalent) |
|---|---|---|
| Arginine | R | 27.3 |
| Histidine | H | 38.3 |
| Lysine | K | 30.3 |
| Aspartic Acid | D | 12.7 |
| Glutamic Acid | E | 15.3 |
| Serine | S | 11.7 |
| Threonine | T | 18.7 |
| Asparagine | N | 14.7 |
| Glutamine | Q | 16.3 |
| Cysteine | C | 24.7 |
| Glycine | G | 11.7 |
| Proline | P | 20.3 |
| Alanine | A | 11.7 |
| Valine | V | 23.3 |
| Isoleucine | I | 32.3 |
| Leucine | L | 27.3 |
| Methionine | M | 34.3 |
| Phenylalanine | F | 52.0 |
| Tyrosine | Y | 50.0 |
| Tryptophan | W | 74.3 |

FIG. 5

| E. coli Gene | Total Cost | AA Length | Average Cost per AA |
|---|---|---|---|
| b2014 | 11447.2 | 452 | 25.3 |
| b1726 | 4657.6 | 178 | 26.2 |
| b3410 | 1724.0 | 78 | 22.1 |
| b2060 | 16194.9 | 720 | 22.5 |
| b4300 | 6201.3 | 260 | 23.9 |
| b0277 | 5261.0 | 208 | 25.3 |
| b1822 | 6479.8 | 269 | 24.1 |
| b1852 | 11659.5 | 491 | 23.7 |
| b4333 | 6732.6 | 286 | 23.5 |
| b2551 | 9556.8 | 417 | 22.9 |
| b0284 | 15969.7 | 732 | 21.8 |
| b1080 | 7372.3 | 365 | 20.2 |
| b3559 | 15737.2 | 689 | 22.8 |
| b2029 | 10771.0 | 468 | 23.0 |
| b4096 | 5086.4 | 226 | 22.5 |
| b3732 | 10288.1 | 460 | 22.4 |
| b1779 | 7419.8 | 331 | 22.4 |
| b1764 | 7632.5 | 347 | 22.0 |

COST-OPTIMIZED DESIGN ANALYSIS FOR RAPID MICROBIAL PROTOTYPING

CROSS-REFERENCE TO RELATED APPLICATIONS

The present application relies on the disclosure of and claims priority to and the benefit of the filing date of U.S. Provisional Application No. 61/739,154, filed on Dec. 19, 2012, the disclosure of which is hereby incorporated by reference herein in its entirety.

BACKGROUND OF THE INVENTION

Field of the Invention

The present invention relates to genome-scale metabolic models for microbial strains. More particularly, the present invention relates to improvements in genome-scale metabolic models that identify and optimize metabolic flux states that minimize the cost of enzyme production while maximizing a desired cellular phenotype such as cellular growth.

Description of Related Art

Petroleum and natural gas are used as the primary raw materials for the manufacturing of most industrial chemicals and polymers. Economic, environmental and geopolitical concerns are driving research efforts to replace fossil fuel-based chemical manufacturing with renewable, bio-based processes that are cheaper, greener and able to be carried out entirely domestically. The key components of these processes will be microorganisms that have been engineered to efficiently carry out a desired metabolism, converting inexpensive carbon substrates (e.g., glucose, $CO_2$, lignocellulosic biomass) to valuable molecular products. In 2003, the successful engineering of Escherichia coli for the production of the monomer 1,3-propanediol by Genencor and DuPont marked an important milestone for metabolic engineering. According to DuPont, biologically produced 1,3-propanediol contributes to about 37% of the mass of Dupont's SORONA polymer fiber and is likely to become the first billion-dollar, non-pharmaceutical industrial biotechnology product. While the 1,3-propanediol bioprocess is a commercialized success, the development of the engineered strain for the process was the result of large investments in time and resources. These investments underscore a need for more efficient bioengineering-based chemical manufacturing processes before these processes can begin to ease the demand for fossil fuels.

Effective design is the hallmark of a mature engineering discipline and necessary for efficient product development. Recent advancements of technologies related to genome-scale characterization (systems biology), construction (synthetic biology) and modeling (computational biology) of biological systems provide the foundation for systems metabolic engineering applications. Experimental methodologies are poised to generate engineered biological strains for a bio-based chemical industry. The main impediment to realizing a bio-based chemical economy is the absence of methods for rigorous biological design (especially that account for multiple scales of biological components). Due to the complexity of cellular networks, the design of (whole-cell) metabolism must be model-guided to be effective.

Figure 1:
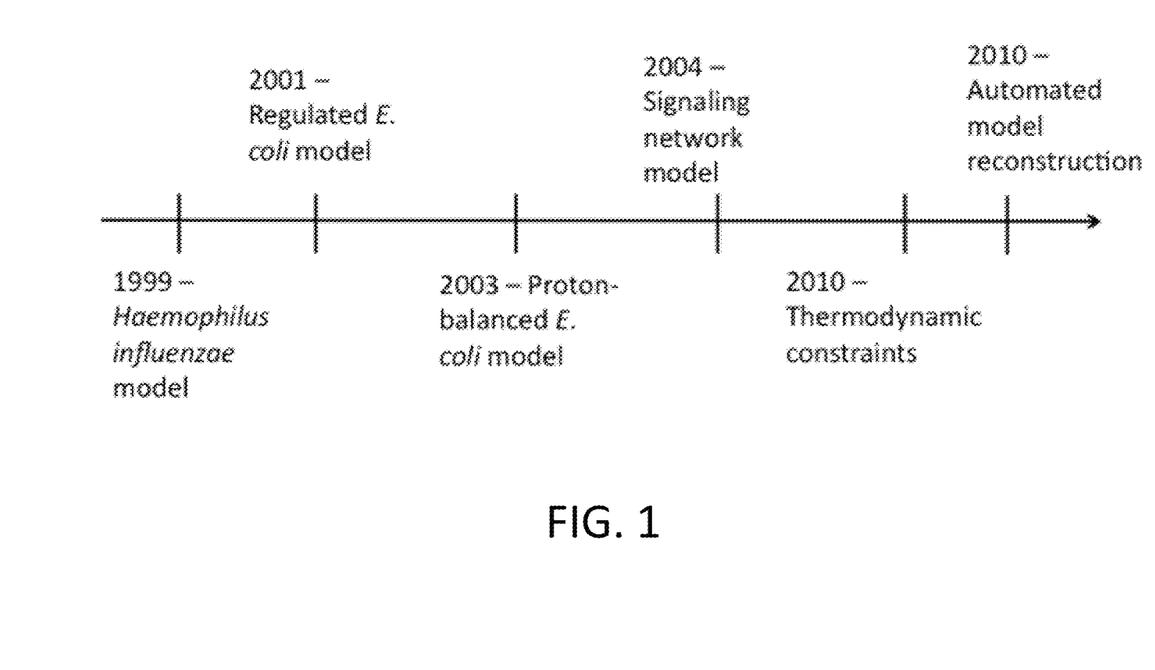
FIG. 1 is a schematic diagram illustrating a timeline of major developments in GSM implementation.
Figure 2:
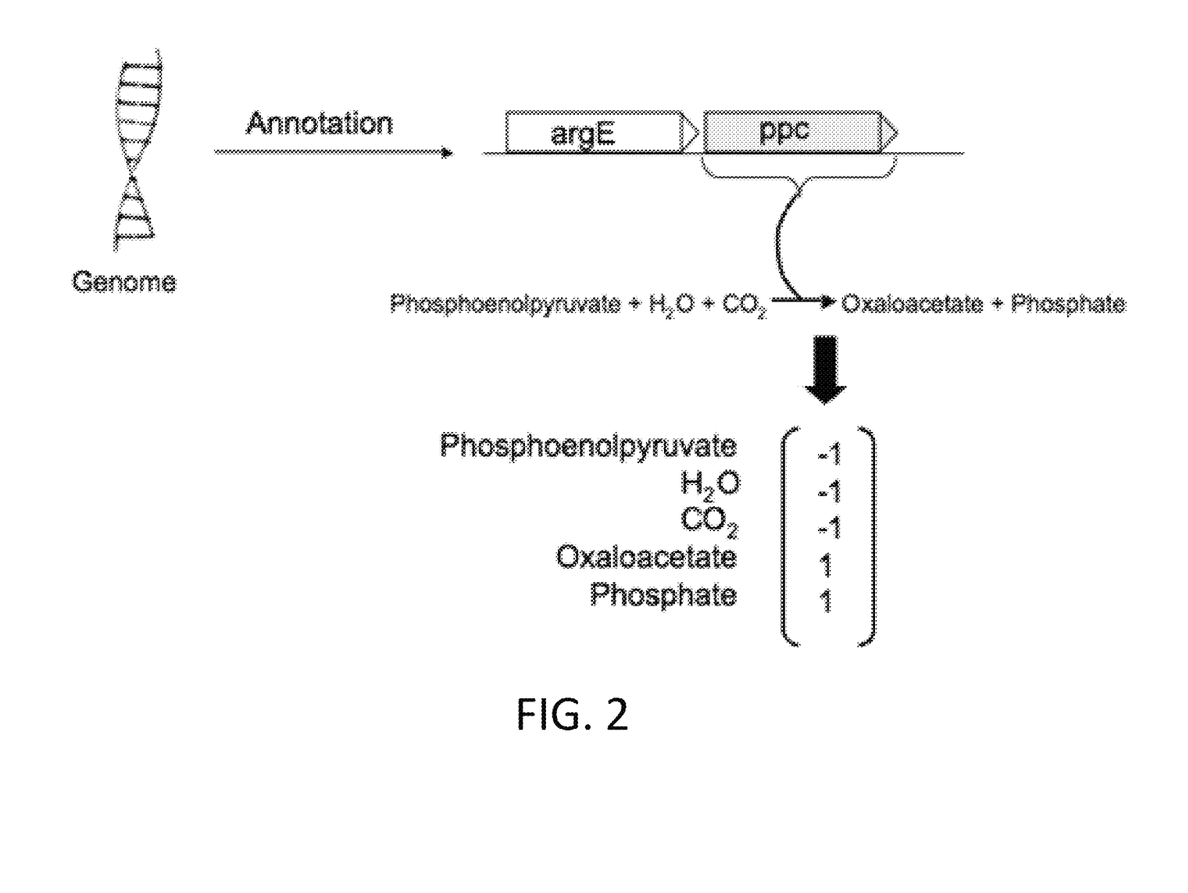
FIG. 2 is a schematic diagram illustrating a genome-scale metabolic model built for *Haemophilus influenza* in 1999.

Current approaches have used genome-scale models (GSMs) of intracellular chemical reactions as a design tool. GSMs are reconstructed from genomic information and the literature and involve steps such as functional annotation of the genome, identification of the associated reactions and determination of their stoichiometry, assignment of localization, determination of the biomass composition, estimation of energy requirements, and definition of model constraints (see Baart G J et al., Genome-scale metabolic models: reconstruction and analysis, Methods Mol Biol. 2012, 799:107-26). FIG. 1 shows a timeline of major developments in GSM implementation. The first genome-scale metabolic model was built for Haemophilus influenza in 1999, establishing the initial approach to genome-scale metabolic modeling (see Edwards J S and Palsson B O, Systems properties of the Haemophilus influenzae Rd metabolic genotype, J Biol Chem. 1999, 274(25):17410-6 ("Edwards and Palsson, 1999")) using the constraint-based modeling approach (see Price N D et al., Genome-scale microbial in silico models: the constraints-based approach. Trends Biotechnol. 2003, 21(4):162-9), illustrated in FIG. 2. Work to add transcriptional regulation to GSMs was published in 2001 for Escherichia coli (see Covert M W et al. Regulation of gene expression in flux balance models of metabolism. J Theor Biol. 2001;213(1):73-88). In 2003 proton balancing of all biochemical reactions was implemented for E. coli (see Reed J L et al., An expanded genome-scale model of Escherichia coli K-12 (iJR904 GSM/GPR), Genome Biol. 2003, 4(9):R54).

Other additions to the genome-scale modeling approach included the formulation of signal transduction pathways (see Papin J A, Palsson B O. Topological analysis of mass-balanced signaling networks: a framework to obtain network properties including crosstalk, J Theor Biol. 2004, 227(2):283-97) and the addition of specification of thermodynamic constraints (see Jol S J, et al., Thermodynamic calculations for biochemical transport and reaction processes in metabolic networks. Biophys J., 2010, 99(10): 3139-44). A semi-automated approach was developed for initial construction of the stoichiometric matrix for new organisms (see Henry C S, DeJongh M, Best A A, Frybarger P M, Linsay B, Stevens RL. High-throughput generation, optimization and analysis of genome-scale metabolic models. Nat Biotechnol., 2010, 28(9):977-82).

After construction of a model, a variety of techniques can be used to analyze a GSM (see Edwards and Palsson, 1999; Schilling C H et al., Towards metabolic phenomics: Analysis of genomic data using flux balances, Biotechnol Progr. 1999; 15(3):288-95; Varma A and Palsson B O, Metabolic Flux Balancing: Basic concepts, Scientific and Practical Use, Bio/Technology. 1994; 12:994-8). Flux-based analysis (FBA) is a common approach for studying GSMs that operates by calculating the flow of metabolites through the metabolic network, thereby enabling the prediction of parameters such as the growth rate of an organism or rate of production of a commercially-significant metabolite (see Orth et al., What is flux balance analysis, Nat. Biotech. 2010 28(3):245-248). Although GSMs have been used in conjunction with flux balance analysis (FBA) to successfully predict such phenotypes to an extent, there are two underlying issues with this approach relevant to metabolic engineering. First, GSMs are underdetermined systems and any FBA solution (a predicted metabolic flux state) is actually one of hundreds of thousands of solutions (alternative flux states) that exhibit the same cellular phenotype. This flexibility makes it difficult to accurately predict actual in vivo metabolic states. Second, computational predictions using growth as a goal are fundamentally at odds with metabolic engineering goals where material and energetic resources are desired to go to a chemical product, not biomass.

The foundations of a genome-scale model (GSM) are the stoichiometric matrix that represents all of the biochemical capabilities and the gene-protein-reaction (GPR) relationships that connect genotype to biochemical phenotype. When using a GSM, simulations are typically run using linear programming algorithms to find solutions that maximize or minimize an objective. The most common objective used is a biomass objective that represents the cellular growth. Simulations that are run to maximize growth assume that cells utilize all of their resources to achieve fastest possible growth. The assumption that cells always seek to maximize growth is not always valid and a study has been conducted to consider additional possible cellular objectives. It has been found that cells do not solely maximize growth. There is at least some component of cellular function that considers energetic costs in terms of ATP (See Schuetz R, et al., Multidimensional optimality of microbial metabolism, Science, 336(6081):601-4). While this computational result may be biologically intuitive, these results point to some limitations in the way in which current GSMs are formulated and employed. These results indicate a shortcoming in the formulation of current GSMs since cellular energetics are only accounted for in a single maintenance pool of ATP that is typically included in the definition of a biomass objective.

Previous efforts in providing methods for metabolic modeling include those described in U.S. Patent Application Publication Nos. 2013/0095566 and 2007/0038419, which references are hereby incorporated by reference herein in their entireties. However, there is currently no mechanism or accounting for the cost of producing individual proteins in a GSM simulation. In the current modeling paradigm, any gene that is identified in the genome is available as a protein in any amount with no consideration given to the cellular cost to produce the protein necessary to carry out a biochemical reaction. There are no preferences or considerations given to the size of a protein or the number of reactions in a pathway. Thus, there is a need for more accurate GSM methods and tools for use in bioengineering applications that account for metabolic expenditures related to protein production.

SUMMARY OF THE INVENTION

To this end, embodiments of the invention provide a computer-implemented method for metabolic modeling that maximizes a cellular phenotype of a modeled organism while minimizing metabolic costs associated with production of individual enzymes involved in metabolic pathways for that phenotype. The addition of considering costs concurrent with function allows for analysis and predictions that are more informative and are more biologically relevant to in vivo cellular function. Without cost considerations, the metabolic model has free utilization of any biochemical function, but realistically, not all functions may be biologically active due to resource and cost considerations.

The cellular phenotype may be growth, production of a metabolite, or any other desirable phenotype. In one embodiment, the maximum cellular growth is obtained as a maximum flux through the set of biomass reactions. Then the minimum cost flux distribution among all possible fluxes that correspond to maximum growth is determined. In embodiments of the computer-implemented method, the stoichiometry of the biomass reaction may be consistent with the amino acid composition of the set of enzymes that participate in the set of reactions for growth. In other embodiments, the activity of each enzyme in the set of enzymes may be determined and a minimum number of proteins that achieve the maximum flux may be calculated based on the enzyme activities. The computer-implemented method may enable modification of genetically encoded biochemical pathways in or to develop engineered microbial strains for the production of high-value chemicals.

According to one embodiment of the invention, a method for identifying and optimizing metabolic flux states that minimize the cost of enzyme production while maximizing a desired cellular phenotype is provided, the method comprising providing a set of reactions for a cellular phenotype; identifying a set of enzymes that participate in the set of reactions for the cellular phenotype; providing the metabolic costs associated with production of each enzyme of the set of enzymes that participates in the set of reactions for the cellular phenotype; identifying a first pool of amino acids and a second pool of amino acids, wherein the first pool of amino acids participate in the set of reactions for the cellular phenotype; and the second pool of amino acids are constituents of the set of enzymes that participate in the set of reactions for the cellular phenotype; maximizing the cellular phenotype by obtaining a maximum flux of the first pool of amino acids through the set of reactions such that one or more and preferably all possible fluxes corresponding to the maximized cellular phenotype are identified; and obtaining a minimum-cost flux distribution of the second pool of amino acids for one or more and preferably each of the possible fluxes corresponding to the maximized cellular phenotype based on the provided metabolic costs; wherein one or more of the above steps are performed through a processor, and whereby performance of the above steps identifies metabolic flux states that simultaneously maximize the cellular phenotype and minimize metabolic costs associated with production of the set of enzymes that participate in the set of reactions for the cellular phenotype.

According to any embodiment of the methods of the invention, the cellular phenotype may be growth and the set of reactions for the particular phenotype may be a set of biomass reactions.

According to any embodiment of the methods of the invention, the cellular phenotype may be the production of a metabolite and the metabolite may be menthol.

According to any embodiment of the methods of the invention, maximum cellular growth may be obtained as the maximum flux through the set of biomass reactions.

According to any embodiment of the methods of the invention, the maximum cellular growth may be obtained by applying a standard flux balance analysis.

According to any embodiment of the methods of the invention, the minimum-cost flux distribution can comprise placing a lower bound on the maximum flux through the set of biomass reactions and replacing the standard flux balance analysis with:

$$\min \sum_{j \in R} c_j v_j$$

wherein R is the set of biomass reactions, $c_j$ is the protein cost for the enzyme that catalyzes reaction j, and $v_j$ is the flux through reaction j.

According to any embodiment of the methods of the invention, the stoichiometry of the biomass reaction may be consistent with the amino acid composition of the set of enzymes that participate in the set of reactions for growth.

According to any embodiment of the methods of the invention, the activity of each enzyme in the set of enzymes may be determined and a minimum number of proteins that achieve the maximum flux may be calculated based on the enzyme activities.

According to other embodiments of the invention, a computer-readable medium is provided that includes instructions that, when executed on a computer, cause a computer to provide a set of reactions for a cellular phenotype; identify a set of enzymes that participate in the set of reactions for the cellular phenotype; provide the metabolic costs associated with production of one or more or each enzyme of the set of enzymes that participates in the set of reactions for the cellular phenotype; identify a first pool of amino acids and a second pool of amino acids, wherein the first pool of amino acids participate in the set of reactions for the cellular phenotype; and the second pool of amino acids are constituents of the set of enzymes that participate in the set of reactions for the cellular phenotype; maximize the cellular phenotype by obtaining a maximum flux of the first pool of amino acids through the set of reactions such that one or more or all possible fluxes corresponding to the maximized cellular phenotype are identified; and obtain a minimum-cost flux distribution of the second pool of amino acids for one or more or each of the possible fluxes corresponding to the maximized cellular phenotype based on the provided metabolic costs; wherein one or more of the above steps are performed through a processor, and whereby performance of the above steps identifies metabolic flux states that simultaneously maximize the cellular phenotype and minimize metabolic costs associated with production of the set of enzymes that participate in the set of reactions for the cellular phenotype.

According to other embodiments of the invention, the computer-readable medium may include instructions that, when executed on a computer, cause a computer to perform any one or more or all steps of any method, in any order, described herein.

According to other embodiments of the invention, a computer comprising the computer-readable medium of the invention is provided.

BRIEF DESCRIPTION OF THE DRAWINGS

The accompanying drawings illustrate certain aspects of embodiments of the present invention, and should not be used to limit or define the invention. Together with the written description the drawings explain certain principles of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

According to one embodiment, the present invention provides a computer-implemented method for identifying and optimizing metabolic flux states that minimize the cost of protein production while maximizing a desired cellular phenotype. According to various aspects of the invention, the computer-implemented method may maximize cellular phenotypes such as growth (biomass) or production of a metabolite, such as a commercially valuable chemical compound, through the selection of metabolic pathways that maximize these phenotypes while minimizing metabolic costs associated with production of the proteomic constituents of individual metabolic pathways.

In one embodiment, two distinct pools of amino acids are used in performing the computer-implemented method, with one pool representing amino acids required for biomass, and the other pool representing amino acids required for the individual metabolic pathways that are used for biomass production. The maximum cellular growth is then obtained as the maximum flux through the biomass reaction using the first pool of amino acids by applying a standard flux balance analysis (FBA). The minimum-cost flux distribution among all possible fluxes that correspond to a maximum growth is then calculated using the second pool of amino acids by considering the amino acid composition of the constituents of the metabolic pathways. The methods described herein and steps thereof provide for the simulation of large (e.g., genomic-scale) biochemical networks, and are thus sufficiently complex that they are preferably implemented by a computer through a set of instructions executed by one or more processors. According to typical embodiments, most or all of the steps of the methods are performed on a computer and thus the methods described herein are considered to be "computer-implemented."

Standard FBA is known in the art and will be briefly summarized here (see Orth et al. 2010 for a more in-depth review and tutorial). The first step required in FBA is to mathematically represent metabolic reactions. This representation includes a tabulation provided as a numerical matrix of the stoichiometric coefficients of each reaction. The flow of metabolites through the network is constrained by these stoichiometries. These constraints may be represented as equations that balance reaction inputs and outputs and as inequalities that impose bounds on the system. The matrix of stoichiometries imposes mass balance, or flux, constraints on the system, such that the total amount of any compound being produced must be equal to the total amount being consumed at steady state. Individual reactions can be given upper and lower bounds that constrain the fluxes of the reaction to a maximum and minimum. If the objective of the FBA is biomass production, the FBA will define the rate at which metabolic compounds are converted to cellular components such as nucleic acids, proteins, and lipids. Mathematically, this objective can be represented by an objective function that indicated how much individual reactions contribute to growth, thereby allowing the FBA to predict growth rates.

Mathematically, metabolic reactions are represented by a stoichiometric matric (S) of size m*n (for a system of m compounds with n reactions). Each row of this matrix represents a unique compound and each column represents one reaction. The stoichiometric coefficients of the metabolites participating in the reaction are entered in each column, with negative coefficients for each metabolite consumed, and positive coefficients for each metabolite produced. The flux through all the reactions is represented by the vector v which has length n. Vector x represents the concentration of all metabolites with length m. At steady state (dx/dt=0), this can be represented mathematically as the product of a matrix of stoichiometry coefficients (stoichiometric matrix S) and the vector of fluxes (v), or:

$$Sv=0$$

Figure 3:
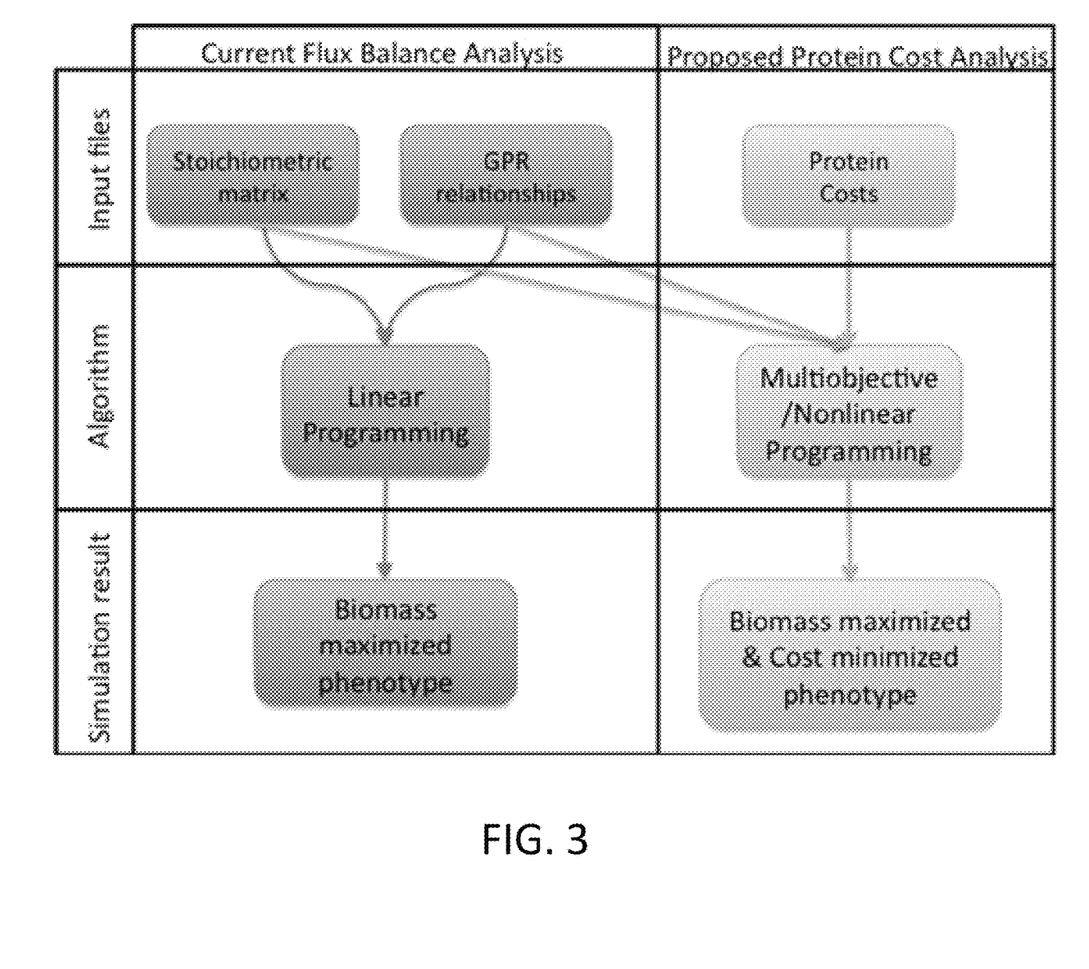
FIG. 3 is a schematic diagram showing a high-level overview of proposed new components to be developed for protein cost analysis in constraint-based models.

FIG. 3 shows a high-level overview of a delineation of existing approaches for analyses of a GSM using FBA and the changes incorporated in the present invention, which may be referred to as Cost-Optimized Design Analysis (CODA). Specifically, there are two typical components for implementing protein production cost analysis in constraint-based models, as shown in FIG. 3. The first is a methodology to calculate protein-specific costs for one or more or preferably every protein in an organism for use in constraint-based model simulations. The second component is the computational algorithm(s) required for integrating protein costs into simulations.

Figure 4:
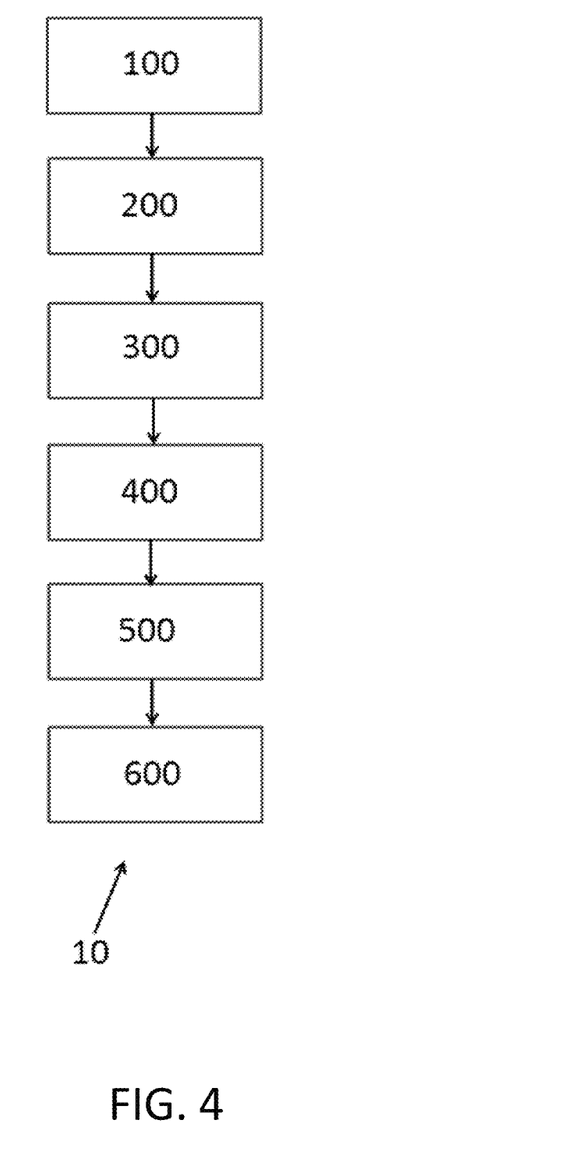
FIG. 4 is a flow chart of an embodiment of a method of the invention.

According to one embodiment, a method for identifying and optimizing metabolic flux states that minimize the cost of protein production while maximizing a desired cellular phenotype is provided. As described below, and as shown in the flow chart of FIG. 4, an embodiment of the method 10 comprises one or more or all of the following steps: calculation of protein-specific costs 100, reformulation of standard model contents 200, algorithm development 300, Phase 1 Algorithmic integration—Multi-objective optimization 400, Phase 2 Algorithmic integration—bi-level optimization 500, and Phase 3 Algorithmic integration—protein kinetics 600.

Methodology

Calculation of Protein-specific Costs 100

Figure 5:
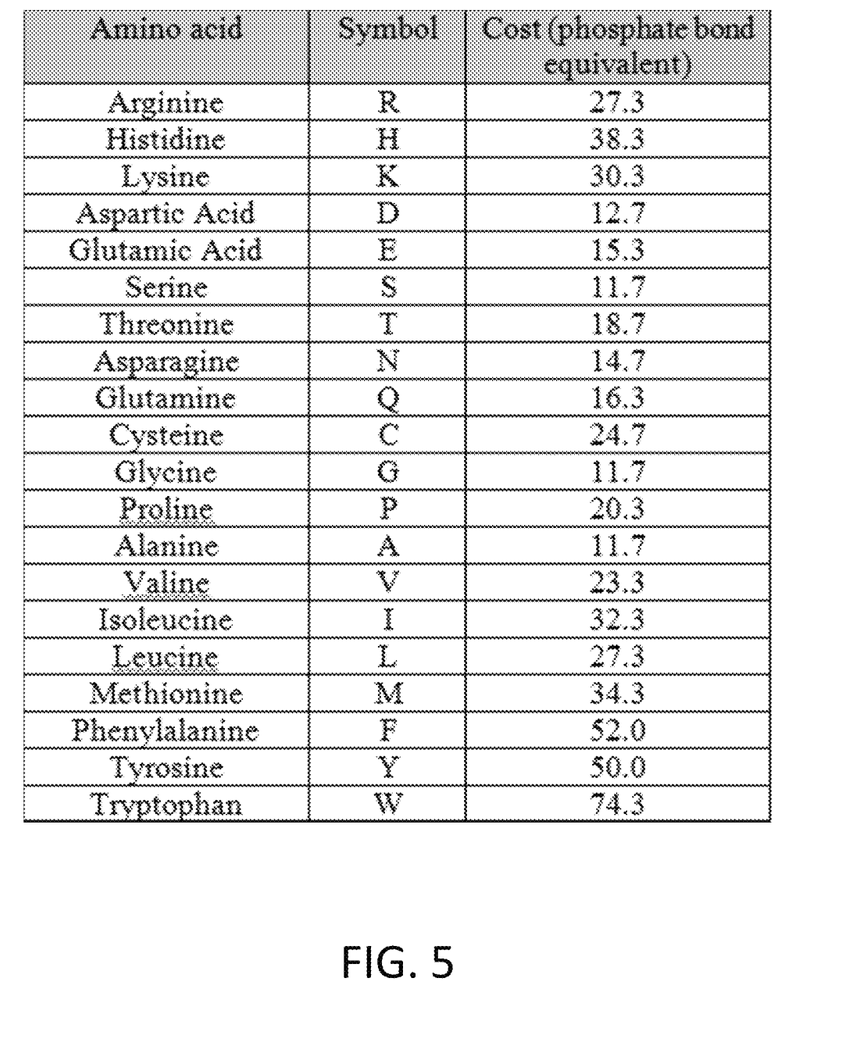
FIG. 5 is a table showing calculated energetic costs (reported as equivalent number of high energy phosphate bonds) for the 20 amino acids commonly used for protein synthesis in prokaryotes.
Figure 6:
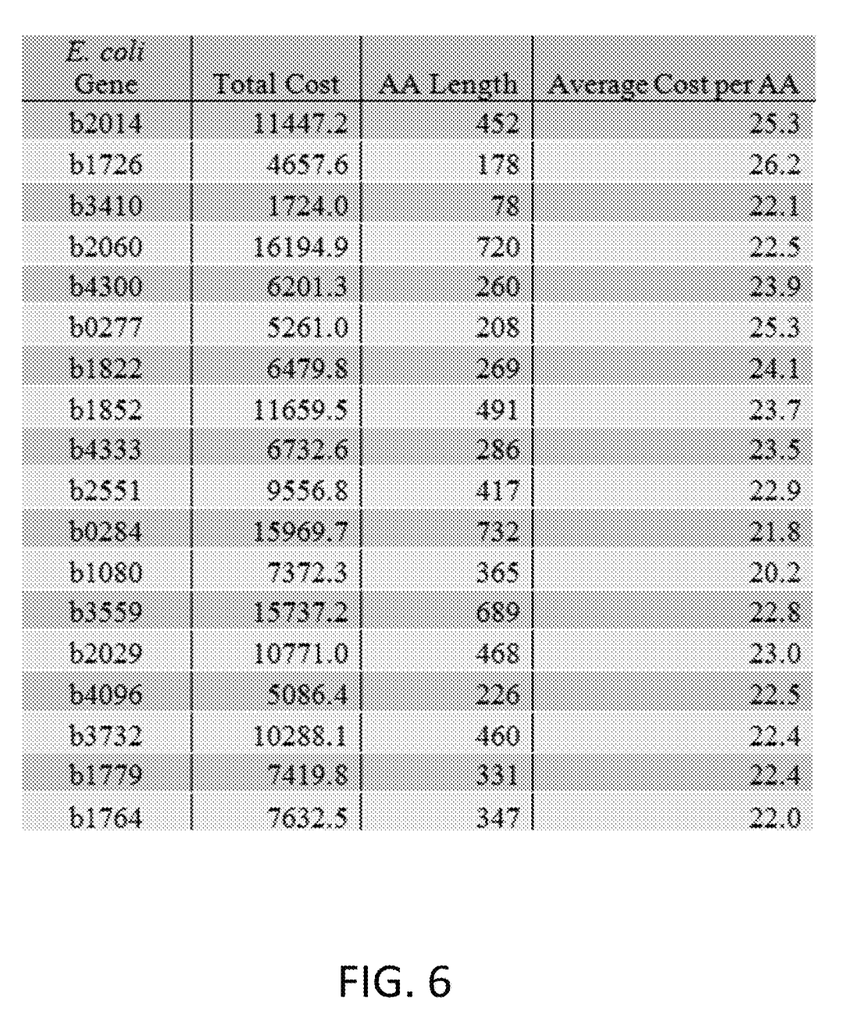
FIG. 6 is a table showing sample calculated synthesis costs for various *E. coli* genes (named by B number).

The first step according to an embodiment of the computer-implemented method of the invention is to calculate the costs of individual proteins. Previous proteomic work has calculated energetic costs for each amino acid in *Escherichia coli* and *Bacillus subtilis* in terms of the energetics of the phosphate bonds and hydrogen atoms contained in each amino acid (see Akashi H and Gojobori T, Metabolic efficiency and amino acid composition in the proteomes of *Escherichia coli* and *Bacillus subtilis*. Proc Natl Acad Sci U S A. 2002, 99(6):3695-700). The results of this study have calculated energetic costs (reported as equivalent number of high energy phosphate bonds) for the 20 amino acids commonly used for protein synthesis in prokaryotes (selenocysteine was not included in the analysis), as shown in the table of FIG. 5. Based upon these calculated costs, the energetic cost for producing an individual protein can be estimated based upon the protein sequence. Sample calculated synthesis costs for various *E. coli* genes (named by B number) are shown in the table of FIG. 6. The costs for each protein can be estimated through data analysis tools such spreadsheet software (e.g. Microsoft Excel) or through scripts developed through a programming language such as Perl based on the calculated energetic costs for the 20 amino acids and the protein sequence.

Reformulation of Standard Model Contents 200

The second step according to an embodiment of the computer-implemented method of the invention is to map protein costs to the correct pathway for use in constraint-based model simulations. In addition, protein stoichiometry involving multimeric homologous domains should be appropriately weighted toward the total reaction-associated cost. To facilitate the inclusion of protein costs in model simulations (especially for existing models), this can be done by generating a new input file with proteins and costs. Current model files with a stoichiometric and gene-protein-reaction (GPR) file will be unchanged.

Algorithm Development 300

Figure 7:
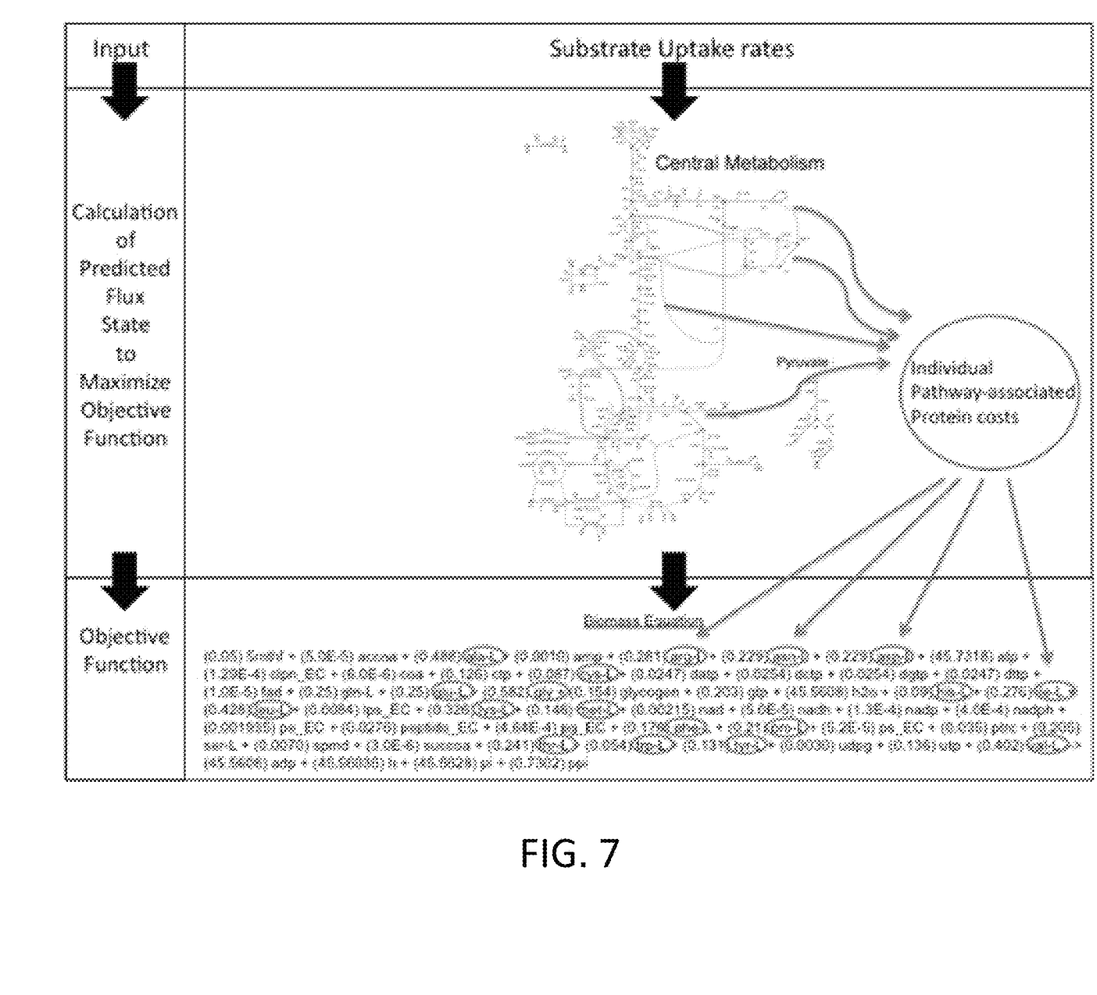
FIG. 7 is a schematic diagram showing components of a GSM simulation highlighting amino acids in the Biomass Objective and the pathway amino acid costs.

Prior art flux balance analysis simulations using genome-scale metabolic models calculate a predicted flux state to maximize or minimize an objective function given input uptake rates and a target objective function (FIG. 7). For the case of cellular growth, a Biomass equation that includes amino acids is used that chemically specifies the requirements needed for growth. In the scenario where growth is the objective and a Biomass equation is used as the objective function, the metabolic flux state is calculated to satisfy the stoichiometry of Biomass equation, including the amino acids stipulated in the Biomass equation. In the prior art, this calculation is not done with consideration given to the actual protein costs or amino acid composition of the pathways that are used.

In accordance with an embodiment of the invention, the protein production cost and amino acid composition of individual proteins are explicitly considered, such that there are two distinct pools of amino acids. The first pool of amino acids are the amino acids that are specified in the Biomass equation. The second pool of amino acids are the amino acids that are required to build the proteins associated with individual biochemical reactions. In the formulation of FBA in the prior art, this second pool of amino acids associated with pathway-specific proteins is not considered. The present invention (or CODA) integrates the protein costs and amino acid composition required for specific biochemical pathways.

There are different methods in which pathway-specific protein costs and protein amino acid composition can be integrated into current modeling approaches. The present disclosure will discuss several embodiments of these methods.

Phase 1 Algorithmic Integration—Multi-objective Optimization 400

In one embodiment, protein costs and protein-specific amino acid composition are integrated by treating the two amino acid pools (amino acids for Biomass and amino acids for pathway-specific proteins) as separate pools. In this case, minimal algorithmic development is necessary to implement a protein cost analysis. The problem becomes one where there are two objectives (growth and protein cost) to consider rather than one objective (growth).

In an exemplary embodiment, an initial cost-based analysis can be performed using a two-step process. In the first step, the maximum cellular growth is obtained as the maximum flux through the biomass reaction. This quantity may be obtained by applying a standard FBA. The second step finds the minimum-cost flux distribution among all possible fluxes that correspond to maximum growth. This distribution is obtained by placing a lower bound on the biomass reaction flux and replacing the FBA objective function with a function that represents the minimization of protein costs:

$$\min \sum_{j \in R} c_j v_j$$

where R is the set of reactions, $c_j$ is the protein cost for the enzyme that catalyzes reaction j, and $v_j$ is the flux through reaction j. The result is a linear program that can be efficiently solved using the same optimization software used for standard FBA simulations.

Figure 8A:
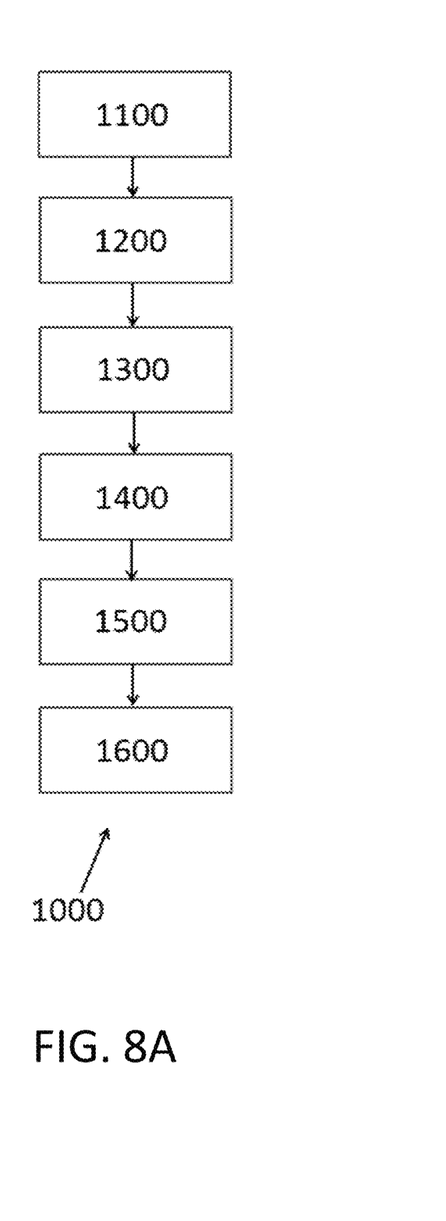
FIGS. 8A and 8B are flowcharts of methods of the invention.

In accordance with an embodiment of the invention, the method provides for identifying and optimizing metabolic flux states that minimize the cost of enzyme production while maximizing a desired cellular phenotype. The method 1000 can be summarized in the flow chart of FIG. 8A. First, a set of reactions for a cellular phenotype is provided, as shown in step 1100. Then, a set of enzymes that participate in the set of reactions for the cellular phenotype is identified, as shown in step 1200. Next, the metabolic costs associated with production of each enzyme of the set of enzymes that participates in the set of reactions for the cellular phenotype are provided, as shown in step 1300. Then, as shown in step 1400, a first pool of amino acids and a second pool of amino acids are identified, wherein the first pool of amino acids participate in the set of reactions for the cellular phenotype; and the second pool of amino acids are constituents of the set of enzymes that participate in the set of reactions for the cellular phenotype. Further, as shown in step 1500, the cellular phenotype is maximized by obtaining a maximum flux of the first pool of amino acids through the set of reactions such that all possible fluxes corresponding to the maximized cellular phenotype are identified. Finally, a minimum-cost flux distribution of the second pool of amino acids for each of the possible fluxes corresponding to the maximized cellular phenotype based on the provided metabolic costs is obtained, as shown in step 1600.

Figure 8B:
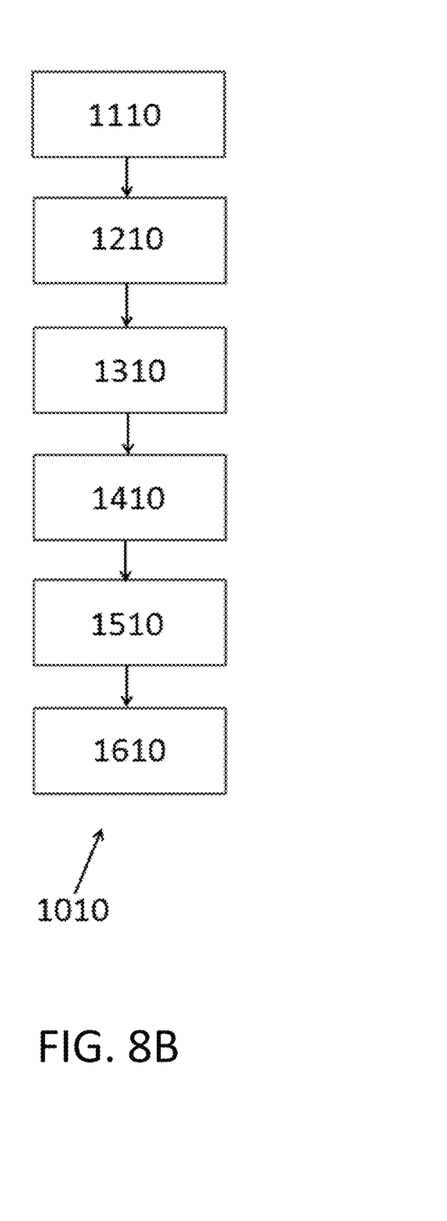

Another embodiment 1010 of the method is shown in FIG. 8B. In accordance with this embodiment, the method provides for identifying and optimizing metabolic flux states that minimize the cost of enzyme production while maximizing cellular growth. First a set of biomass reactions is provided, as shown in step 1110. Then, a set of enzymes that participate in the set of biomass reactions is identified, as shown in step 1210. Next, the metabolic costs associated with production of each enzyme of the set of enzymes that participates in the set of biomass reactions are provided, as shown in step 1310. Then, a first pool of amino acids and a second pool of amino acids are identified in step 1410, wherein the first pool of amino acids participate in the set of biomass reactions; and the second pool of amino acids are constituents of the set of enzymes that participate in the set of biomass reactions. Further, as shown in step 1510, cellular growth is maximized by obtaining a maximum flux of the first pool of amino acids through the set of biomass reactions such that all possible fluxes corresponding to maximized cellular growth are identified. As shown in step 1610, a minimum-cost flux distribution of the second pool of amino acids for each of the possible fluxes corresponding to maximized cellular growth based on the provided metabolic costs is obtained.

One or more of the steps of embodiment 1000 or embodiment 1100 may be performed through a data processing device such as a processor. Further, the steps of embodiment 1000 or embodiment 1100 need not be performed in the order as shown. For example, the step of providing metabolic costs 1300 or 1310 may be performed later in the process, up until after steps 1500 and 1510. Further, some steps may be deleted and/or other steps may be added at any point in the flowchart. Variations of the method shown that fall into the scope of the present invention can be appreciated by a skilled artisan.

Phase 2 Algorithmic Integration—Bi-level Optimization 500

One of the main limitations of implementing a cost-based analysis using multi-objective optimization is that the two amino acid pools are handled and considered separately. In a theoretical sense, the amino acid stoichiometry that is included in the Biomass equation should directly relate to the amino acid composition of a cell at any time point. Thus, amino acid stoichiometry in the Biomass equation should directly reflect the amino acid composition of proteins that are expressed and used in the cell. If pathway usage changes, then at the same time, the stoichiometry of the Biomass equation should change to reflect the change in protein (and amino acid) composition.

In another embodiment, an additional level of detail can be added to protein cost analysis by linking the amino acid composition such that the stoichiometry of the Biomass equation and the actual composition of proteins that are used are consistent. When adding the consideration of protein production costs associated with each amino acid, this becomes a bi-level optimization problem, where the cell is maximizing the benefit of growth subject to the condition that growth is maximized. The benefit of an amino acid is quantified based on both the potential contribution to growth and the cost of production. The outer optimization problem has an additional constraint enforcing an energy "budget" for the cell. Note that in this framework, the stoichiometry of the biomass reaction adapts based on the benefit/cost of amino acids.

Bi-level optimization has been previously used with constraint-based models to consider two objectives for metabolic engineering applications. The implementations of bi-level optimization such as OptKnock (see Burgard et al., Optknock: a bilevel programming framework for identifying gene knockout strategies for microbial strain optimization, Biotechnology and Bioengineering, 2003; 84-647-657) and OptStrain (see Pharkya P et al., OptStrain: a computational framework for redesign of microbial production systems, Genome Res. 2004 November; 14(11):2367-76) were developed to consider maximum production of a chemical compound while still maintaining all of the requirements for cellular growth. In these methods, the bioengineering objective is pitted against the cellular objective. In embodiments of the computer-implemented method of the invention, the benefits and energy requirements imposed by "nature" for amino acids are pitted against the cellular objective of growth.

As with the previous methods applying bi-level optimization to analysis of metabolic networks, the inner optimization problem is a linear program that is equivalent to FBA for a given stoichiometry of the biomass reaction. The bi-level problem can be converted into a single level nonconvex optimization problem by requiring that the inner problem have an objective function equal to its dual. The single level problem has a linear objective and a mix of linear constraints and quadratic nonconvex constraints.

Phase 3 Algorithmic Integration—Protein Kinetics 600

In another embodiment, the contribution of individual protein kinetics can be added to protein cost analyses as a third level of detail. For every reaction that is predicted to actively carry a metabolic flux, there will be a minimum amount of expressed protein associated with the calculated pathway flux. The number of proteins required will vary depending upon the specific enzymatic activity of the protein.

If the enzymatic kinetic activity of a protein is known, then a minimum number of proteins can be calculated to achieve the predicted pathway flux. In the scenarios considered above, it is beneficial to consider the simplified scenario where any expressed protein has sufficient activity to support the calculated metabolic flux to allow for development of the basic algorithms and overall approach. As a last step of the analysis, specific enzyme activity can be integrated for any proteins where enzymatic activity has been characterized.

In this step, the benefits/costs of growth will not be limited to the amino acids in the biomass reaction, but are accounted additionally for all proteins required for catalyzing reactions in the metabolic network. The outer optimization of the bi-level optimization problem of the previous step is modified to account for the new costs. The problem may be converted to a single-level problem using the same methods as for Phase 2.

Computer-Executable Instructions

It will be understood that the various methods, processes, and operations of the present invention described and/or depicted herein may be carried out by a group of computer-executable instructions that may be organized into routines, subroutines, procedures, objects, methods, functions, or any other organization of computer-executable instructions that is known or becomes known to a skilled artisan in light of this disclosure, where the computer-executable instructions are configured to direct a computer or other data processing device such as a processor to perform one or more of the specified processes and operations. The computer-executable instructions may be written in any suitable programming language. A number of programming languages are known that can be used to write software for performing the computational methods described herein, including MATLAB (The Mathworks, Inc., Natick, Mass.) and Python. FBA computations fall into the category of constraint-based reconstruction and analysis (COBRA) methods; the COBRA Toolbox (see Becker SA, et al. Quantitative prediction of cellular metabolism with constraint-based models: The COBRA Toolbox. Nat. Protocols. 2007, 2:727-738; Schellenberger et al., Quantitative prediction of cellular metabolism with constraint-based models: the COBRA Toolbox v2.0. Nature Protocols 2001, 6:1290-1307) is a freely available MATLAB toolbox that can be used to perform a variety of COBRA methods, including many FBA-based methods. A Python version is also available (see Ebrahim A et al., COBRApy: COnstraints-Based Reconstruction and Analysis for Python, 2013, BMC Syst Bio 7:74). Both versions are available at http://systemsbiology.ucsd.edu/Downloads/Cobra_Toolbox.

Computer-Readable Medium

Embodiments of the invention also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to implement a process for identifying metabolic flux states that minimize the cost of protein production while maximizing a desired cellular phenotype such as those described herein. The processor, through the computer-executable instructions, may maximize cellular phenotypes such as growth (biomass) or production of a metabolite, such as a commercially valuable chemical compound, through the selection of metabolic pathways that maximize these phenotypes while minimizing metabolic costs associated with production of the proteomic constituents of individual metabolic pathways. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising any combination of software, hardware, or firmware.

Computers or Devices

Embodiments of the invention include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, and operations of the invention. The computer or device performing the specified calculations, processes, steps, and operations may comprise at least one processing element such as a central processing unit (i.e. processor) and a form of computer-readable memory which may include random-access memory (RAM) or read-only memory (ROM). The computer-executable instructions can be embedded in computer hardware or stored in the computer-readable memory such that the computer or device may be directed to perform one or more of the processes and operations depicted and/or described herein.

Computers Systems

Additional embodiments of the invention comprise a computer system for carrying out the method of the invention. The computer system may comprise a processor for executing the computer-executable instructions, one or more databases, a user interface, and a set of instructions (e.g. software) for carrying out the method. The computer system can be a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network.

The information in the database(s) can include information on one or more metabolic reactions for at least one organism. This may include the set of enzymes, substrates, and products for each reaction and their stoichiometries, annotations for each enzyme, such as descriptions of functional information, and biological sequence/structure information on constituents of the reactions, including without limitation genomic sequence information, mRNA sequence information, protein sequence information, and information on secondary and tertiary structures. The information in the database may include information on a set of reactions that may make up a biochemical network for a particular organism. The information may include metabolic reactions making up biochemical reactions for microbes, plants, or animals. Further, the information may be divided categorically into separate databases, such as one database may house sequence information, another database may house annotations, and one database may house information on individual metabolic reactions.

The database can be a flat file database or a relational database. The database may be an internal database, such as that maintained by a private entity and typically maintained behind a firewall, or an external database, such as one that is made accessible to users through the World Wide Web. Various external databases for housing information on sequences, functional annotations, or reactions making up biochemical networks are known. These include sequence databases including GenBank, GenPept, RefSeq, Swiss-Prot, PIR, PRF, and PDB, comprehensive databases on genes and proteins that include functional annotations such as GeneCards and UniProt, and databases with biochemical pathway information such as EcoCyc, KEGG, WIT, and EMP.

The user interface may be a graphical user interface which may be used in conjunction with the computer-executable code and databases. For example, the graphical user interface may allow a user to select one or more biochemical reactions or networks for comparison and/or optimization, or may be capable of displaying results of the computer-implemented method of the invention. The graphical user interface may allow a user to perform these tasks through the use of text fields, check boxes, pull-downs, command buttons, and the like. The interface may provide access to information in internal databases or include links to external databases such as those described herein. A skilled artisan will appreciate how such graphical features may be implemented for performing the tasks of the invention.

Such graphical controls and components are reusable class files that are delivered with a programming language. For example, pull-down menus may be implemented in an object-oriented programming language wherein the menu and its options can be defined with program code. Further, some programming languages integrated development environments (IDEs) provide for a menu designer, a graphical tool that allows programmers to develop their own menus and menu options. The menu designers provide a series of statements behind the scenes that a programmer could have created on their own. The menu options may then be associated with an event handler code that ties the option to specific functions. Text fields, check boxes, and command buttons may be implemented similarly through the use of code or graphical tools. A skilled artisan can appreciate that the design of such graphical controls and components is routine in the art.

Applications

The present invention may be used as a design principle for computationally designing strains for chemical production. This is a critical component for the production of specialty chemicals that involve branching pathways that incur costs to be expressed and functional, but do not contribute directly to cellular fitness/growth. Thus, when designing specialty chemical pathways, a theoretical calculation may fail to be functional in a cell as it may be too metabolically expensive to be expressed. The invention may also be used to study and address metabolic costs associated with expression of virulence/pathogenicity in microbial pathogens, plausibly informing routes to treat or prevent infection.

Figure 9:
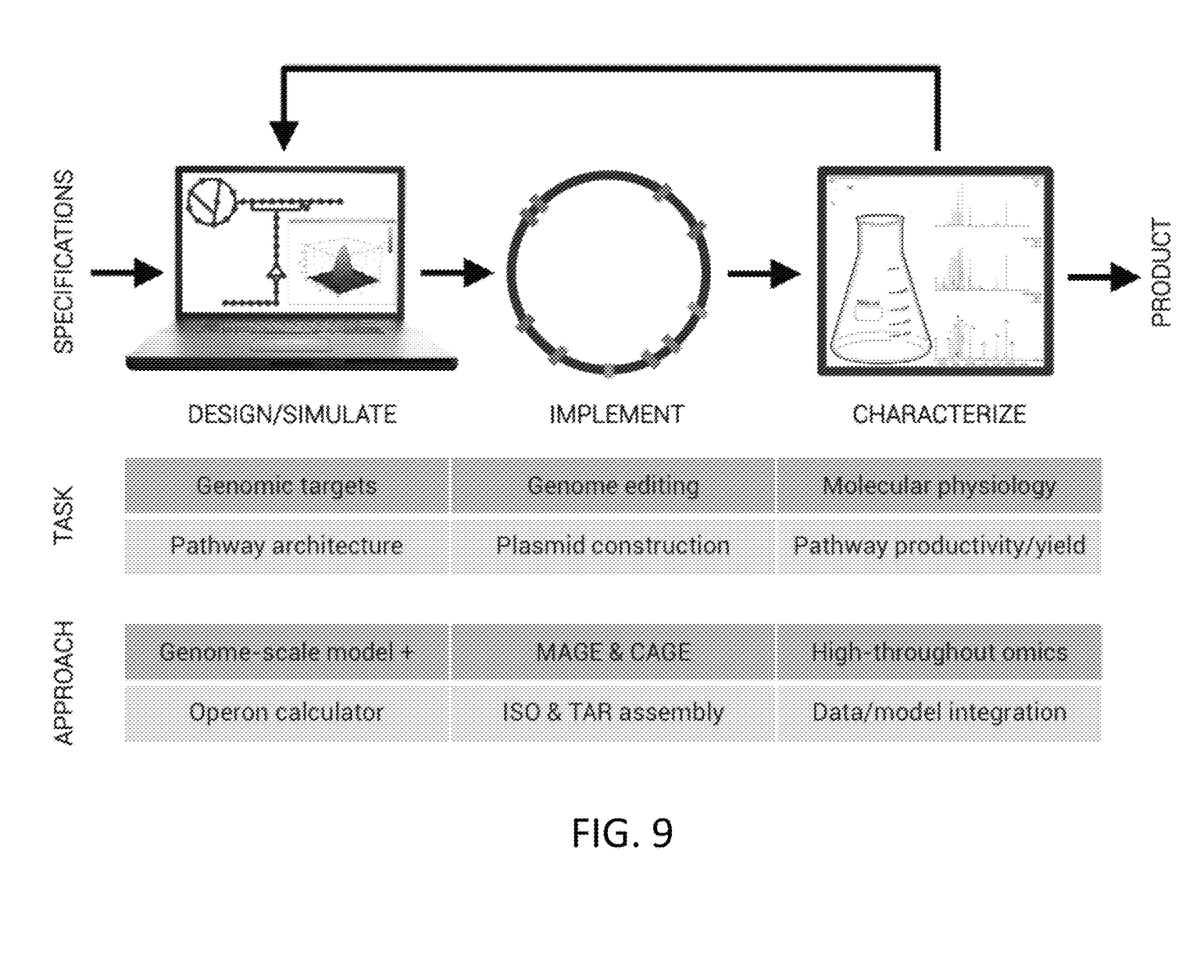
FIG. 9 is a schematic diagram showing development of microbial strains through an iterative process of design, implementation and characterization at the global scale (top rows) and local scales (bottom rows).

The general approach to developing an engineered microbial strain is shown in FIG. 9, with delineations made between global-scale design and implementation (coarse-tuning) and local-scale design and implementation (fine-tuning). Coarse-tuning can be used to refer to modifying higher-level biological functions that change overall network topology such as adding or deleting specific biochemical reactions (including the enzymes the carry out the transformation and the genes that encode the enzymes). Fine-tuning can be used to refer to modifying exact DNA sequences of regulatory elements (e.g., promoters, 5' untranslated regions) and coding sequences (e.g., codon optimization) that result in regulating pathway steps (i.e., how much, when, where). The coarse-tuning and fine-tuning can be carried out by a metabolic engineer based on the results of the computer-implemented methods of the invention. That is, metabolic pathways which maximize a desired phenotype, such as growth or production of a metabolite, while minimizing the costs of product of proteins involved in the metabolic reactions, can be determined using the computer-implemented methods of the invention, and the metabolic engineer can manipulate the genome of the microbial strain through coarse-tuning and/or fine-tuning to correspond to the results of the computer-implemented methods.

Global-scale considerations involve the design and analysis of genes, proteins, and biochemical reactions such as through the methods of the invention as the first critical design step that is required to modify and engineer cellular function. This aspect can be considered a coarse adjustment that is intended to establish the proper initial conditions and achieve the majority of the functional response desired. Coarse-tuning microbial metabolism for chemical production is achieved by analysis and manipulation of metabolic pathways based on data resulting from the methods of the invention and often can utilize systems biology methodologies.

Local-scale considerations analyze specific DNA sequences required for experimental implementation and are the second critical design step required to modify and engineer cellular function. This aspect is considered to be a fine adjustment that is intended to work within the context of a design to improve the functional response. Local-scale design and implementation for chemical production is achieved by genetic tools (e.g., engineered mRNA secondary structure) and can involve many synthetic biology methodologies.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. Where a value is provided, or an endpoint for a range is provided, such values and/or endpoints can be used with other specified values and/or endpoints to establish additional ranges that fall within the scope of the invention. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure, such as non-patent literature, the content provided at listed website addresses, pending patent applications, published patent applications, and published patents, are each individually incorporated by reference herein in their entireties and as such are intended to provide an efficient way of supplementing the enabling disclosure of this invention as well as provide background detailing the level of ordinary skill in the art.

The invention claimed is:

1. A method for optimizing a phenotype in an actual microbial strain, the method comprising:
   simulating metabolic flux states by steps comprising:
      providing a set of reactions for a cellular phenotype;
      identifying a set of enzymes that participate in the set of reactions for the cellular phenotype;
      providing the metabolic costs associated with production of each enzyme of the set of enzymes that participates in the set of reactions for the cellular phenotype;
      identifying a first pool of amino acids which participate in the set of reactions for the cellular phenotype;
      identifying a second pool of amino acids which are constituents of the set of enzymes that participate in the set of reactions for the cellular phenotype;
      maximizing the cellular phenotype by obtaining a maximum flux of the first pool of amino acids through the set of reactions such that all possible fluxes corresponding to the maximized cellular phenotype are identified;
      obtaining a minimum-cost flux distribution of the second pool of amino acids for each of the possible fluxes corresponding to the maximized cellular phenotype based on the provided metabolic costs;
      whereby individual metabolic pathways that maximize the cellular phenotype while minimizing metabolic costs associated with production of the set of enzymes that participate in the set of reactions for the cellular phenotype are identified; and
   implementing results of the simulation by:
      providing an actual microbial strain and modifying the actual microbial strain to maximize the cellular phenotype of the actual microbial strain by manipulating the genome of the actual microbial strain to add or delete genes encoding specific biochemical reactions corresponding to the individual metabolic pathways that were identified to maximize the cellular phenotype while minimizing metabolic costs in the simulation.

2. The method of claim 1, wherein the cellular phenotype is growth and the set of reactions for the particular phenotype is a set of biomass reactions.

3. The method of claim 2, wherein the maximum cellular growth is obtained as the maximum flux through the set of biomass reactions.

4. The method of claim 3, wherein the maximum cellular growth is obtained by applying a flux balance analysis.

5. The method of claim 4, wherein obtaining a minimum-cost flux distribution comprises placing a lower bound on the maximum flux through the set of biomass reactions and replacing the standard flux balance analysis with:

$$\min \sum_{j \in R} c_j v_j$$

wherein R is the set of biomass reactions, $c_j$ is the protein cost for the enzyme that catalyzes reaction j, and $v_j$ is the flux through reaction j.

6. The method of claim 2, wherein the stoichiometry of the biomass reaction is consistent with the amino acid composition of the set of enzymes that participate in the set of reactions for growth.

7. The method of claim 1, wherein the cellular phenotype is production of a metabolite.

8. The method of claim 7, wherein the metabolite is menthol.

9. The method of claim 1, further comprising determining the activity of each enzyme in the set of enzymes and calculating a minimum number of proteins that achieve the maximum flux based on the enzyme activities.

10. The method of claim 1, wherein modifying the actual microbial strain comprises manipulating one or more metabolic pathways of the actual microbial strain.

11. The method of claim 1, wherein modifying the actual microbial strain comprises adding or deleting specific biochemical reactions.

12. The method of claim 1, wherein modifying the actual microbial strain comprises modifying DNA sequences of regulatory elements and coding sequences that result in regulating pathway steps.

13. The method of claim 1, wherein modifying the actual microbial strain comprises modifying or engineering cellular function.

14. The method of claim 1, wherein modifying the actual microbial strain comprises engineering mRNA secondary structure.

* * * * *